(12) United States Patent
Makoui et al.

(10) Patent No.: US 6,569,274 B1
(45) Date of Patent: May 27, 2003

(54) SEALABLE NONWOVEN WEB

(75) Inventors: Kambiz Bayat Makoui, Allentown, PA (US); Joel Erwin Goldstein, Allentown, PA (US)

(73) Assignee: Air Products and Chemicals, Inc., Allentown, PA (US)

( * ) Notice: Subject to any disclaimer, the term of this patent is extended or adjusted under 35 U.S.C. 154(b) by 877 days.

(21) Appl. No.: 09/017,375

(22) Filed: Feb. 2, 1998

Related U.S. Application Data

(63) Continuation-in-part of application No. 08/852,626, filed on May 7, 1997, now Pat. No. 5,961,763.

(51) Int. Cl.$^7$ ............................................. B32B 31/00
(52) U.S. Cl. ................... 156/204; 156/209; 156/226; 156/276; 156/306.3; 156/308.2; 156/308.6; 156/309.6
(58) Field of Search ............................ 156/276, 308.2, 156/309.6, 308.6, 204, 226, 209, 306.3

(56) References Cited

U.S. PATENT DOCUMENTS

| | | | |
|---|---|---|---|
| 3,575,749 A | | 4/1971 | Kroyer |
| 4,102,340 A | | 7/1978 | Mesek et al. |
| 4,260,443 A | | 4/1981 | Lindsay et al. |
| 4,590,102 A | * | 5/1986 | Rosamillia et al. ...... 427/374.1 |
| 4,600,458 A | * | 7/1986 | Kramer et al. .......... 156/276 X |
| 5,273,596 A | | 12/1993 | Newkirk |
| 5,370,764 A | | 12/1994 | Alikhan |
| 5,415,717 A | | 5/1995 | Perneborn |

FOREIGN PATENT DOCUMENTS

| | | |
|---|---|---|
| EP | 0202472 | 11/1986 |

* cited by examiner

*Primary Examiner*—Jeff H. Aftergut
(74) *Attorney, Agent, or Firm*—Russell L. Brewer; Mary E. Bongiorno

(57) ABSTRACT

Disclosed is a process for producing a laminate suited for use in producing disposable absorbent products comprising a nonwoven web formed from randomly dispersed fibers bonded with a crosslinked vinyl acetate/ethylene adhesive and a particulate polymeric absorbent entrapped within the laminate in fixed location by means of adhesively bonding the nonwoven web to itself or to another substrate, the improvement which comprises utilizing a nonwoven web incorporating an acrylic or vinyl acetate/ethylene adhesive having the following characteristics, and further, said nonwoven web adhesively bonded to itself or to another substrate through the crosslinked acrylic or crosslinked vinyl acetate/ethylene adhesive.

9 Claims, No Drawings

SEALABLE NONWOVEN WEB

CROSS-REFERENCE TO RELATED APPLICATIONS

This application is a continuation-in-part of U.S. Ser. No. 08/852,626 filed May 7, 1997, now U.S. Pat. No. 5,961,763 the subject matter being incorporated by reference.

STATEMENT REGARDING FEDERALLY SPONSORED RESEARCH OR DEVELOPMENT

Not applicable.

BACKGROUND OF THE INVENTION

Over the past two decades or so, a variety of disposable absorbent products have been widely marketed for use as disposable baby and adult diapers, underpads, hospital bed pads, feminine napkins, and so forth. These products largely consist of laminates of one or more layers of tissue-like material incorporating a layer of liquid absorbing agent. Typically, these laminates are constructed of a nonwoven cover sheet, an absorbent center section and a water impermeable backing sheet to entrain moisture within the disposable absorbent product.

In recent years, a variety of hydrocolloidal polymers, often referred to as superabsorbents, have been incorporated into these laminates for disposable absorbent products. Prior to the incorporation of superabsorbents, it was common to incorporate tissue-like cellulose and other bulky, water absorbing materials to absorb body fluids. Superabsorbents have been used to replace at least a portion of the cellulosic materials primarily because these polymeric components have an ability to absorb larger quantities of liquids, thereby enhancing the effectiveness of the disposable product. Another factor leading to their use is their ability to retain moisture under pressure as might be experienced when a child sits on the absorbent medium. Cellulose, waddings and fluff pulp tend to fail under those types of pressure conditions.

The introduction of superabsorbents into the disposable absorbent product market has not been without problems. The superabsorbents are dusty thus making handling and storage difficult and they tend to shift within the finished product. Shifting of the superabsorbent presents two problems, first the superabsorbent may shift from the point where it is most needed in the product and second, shifting allows the superabsorbents to agglomerate within the product. When the superabsorbents agglomerate, they display a tendency to generate a gelatinous barrier film when wet which detracts from their ability to absorb fluids. To overcome shifting of the superabsorbents within these laminates for disposable absorbent soft goods, a variety of methods have been developed to retain the superabsorbents in fixed location within the laminates. Typically, these methods of retaining the superabsorbents within a fixed position within the laminates (typically the fixed locations have been in the shape of squares, rectangles, and triangles) have involved the application of a variety of adhesives, the use of hot melts, specialty fibers, or superabsorbents which are moisture activated, to anchor the superabsorbent between fibrous facing sheets.

The following patents are representative of various techniques for preparing a variety of disposable absorbent soft goods and fixing superabsorbents and hydro-colloidal polymers within the disposable product.

U.S. Pat. No. 4,102,340 discloses an absorbent article, such as a diaper or sanitary napkin, comprised of a facing sheet, an absorbent pad means and a moisture-impervious backing sheet. The absorbent pad comprises a fibrous structure having an intermediate, densified layer and a layer of highly porous, loosely compacted bats on each side of the densified layer, the bat incorporating particulate water insoluble and water swellable polymeric absorbents. The facing sheet is comprised of a cellulosic material incorporating a self-crosslinking acrylic emulsion bonding agent to supply strength to the cellulosic substrate such that when the disposable product is wet it retains dimensional stability. In practice, the absorbent pad is disposed between the moisture impervious backing, and the facing sheet and then bonded to the moisture-impervious backing sheet by means of adhesive beads.

European 0 202 472 discloses non-laminated, dry formed absorbent products formed by an air-laying technique. More particularly, the absorbent products are formed by forming in dry condition, a sheet or web from matrix fibers consisting of cellulose or mixture of cellulosic and synthetic fibers. Distributed among the matrix fibers is a superabsorbent material and a heat-activated binder such as polyvinyl acetate, vinyl acetate ethylene and vinyl chloride, etc., which, upon the application of heat, thermally sets to bind the matrix fibers and liquid absorbing material into a coherent web.

U.S. Pat. No. 4,260,443 discloses a process for producing disposable absorbent goods which comprises forming a laminated sheet composed of two or more layers of tissue having a water-absorbing polymer, e.g., a superabsorbent, fixed in place between the layers. When the tissue sheets are passed through an embossing roll, a, small amount of water is applied to all, or a percentage of the embossed area, which causes the superabsorbent to become tacky and act as an adhesive at these locations thereby securing the tissue sheets together. After the resulting laminate has passed through the embossing roll, the laminating sheet is dried.

U.S. Pat. No. 3,575,749 discloses a method for making fibrous sheets or web by incorporating a binder such as starch or starch derivative, acrylic or butadiene/styrene emulsions, etc. into the fibrous material. The fiber layer to which the binder has been applied is made plastic by applying moisture. During an embossing operation where the fibers are brought into intimate contact with each other followed by drying of the product, the partly plasticized binder is cured, thereby effecting a strong bond.

U.S. Pat. No. 5,273,596 discloses a method for producing disposable absorbent pads employing a multi-layer, nonwoven fabric for use as a top sheet. The multi-layer, fabric is comprised of a continuous first layer of about 75% hydrophobic thermoplastic fibers and a second layer comprised of a blend of hydrophobic and hydrophilic fibers. The layers are secured by bonds which are formed by melt-fusing portions of the hydrophobic thermoplastic fiber.

U.S. Pat. No. 5,415,717 discloses an apparatus for depositing particles on a moving web of materials. In the process, a web is conveyed by means of a belt and particulate material, e.g., a superabsorbent, is deposited upon the web. As the web is conveyed along the belt, it is brought into contact with a second web and the second web is caused to overlap the particulate particles. The first and second webs then are compressed beneath rollers and the particles caused to be locked into a fixed position through the use of binder coatings or spray adhesives.

U.S. Pat. No. 5,370,764 discloses a process for producing film-laminated material employing a nonwoven web formed by a variety of processes such as spun bonding, air laying, wet laying, dry laying, etc. The laminates incorporate a moisture-absorbing medium and, when brought into contact with another web, are embossed to form spaced apart bonding regions. Bonding is effected via thermal means, e.g., heated rollers and the like.

BRIEF SUMMARY OF THE INVENTION

This invention relates to an improvement in a process for producing a laminate for use in preparing disposable absorbent products. Such laminates are comprised of a nonwoven fibrous web bonded by means of a polymeric resin, particularly a crosslinkable polymeric resin, particulate, polymeric absorbent (superabsorbent) in fixed position within the laminate. The improvement resides in utilizing a nonwoven web bonded with a slightly pressure sensitive vinyl acetate/ethylene polymer having a $T_g$ of −22.0 to ±4° C. and using the adhesiveness afforded within the nonwoven web itself for anchoring the superabsorbents within a fixed position at room temperatures, e.g., from 20 to 30° C. Anchoring is effected by applying localized pressure to the nonwoven web. In another embodiment the $T_g$ can be from −22 to +18° C. and anchoring can be effected by applying pressure to the nonwoven web and minimal heat to effect an adhesive temperature below about 100° C., preferably from 60 to 100° C., and thus in the absence of the substantial heat required for melting thermal fusible thermoplastic fibers, and in the absence of applied moisture. Additionally, the adhesion is effected in the absence of applied moisture. Substrates essentially devoid of thermofusible fibers which require temperatures higher than 105° C. to melt and effect adhesion, can be used to form the laminates.

The nonwoven web when utilized in the manufacture of laminates for disposable absorbent products incorporating superabsorbents within fixed locations within the laminate product allows for the following advantages:

- an ability to effect excellent adhesion with the application of heat and pressure at temperatures below the fusion temperature of conventional themobondable plastics and polymeric olefins employed in personal care products, e.g., below a temperature of about 105° C.;
- an ability to effect sufficient adhesion between the nonwoven web and another substrate, including itself, without additional adhesive or the addition of water and yet retain sufficient strength;
- an ability to simplify the process for producing a laminate used in producing disposable absorbent products by eliminating process steps associated with the application of a moisture activated adhesive and/or the elimination of the step of applying water;
- an ability to wind the laminates into large rolls and then unwind such laminates without tearing or deforming due to adhesion to itself;
- an ability to reduce energy costs associated with the manufacture of laminates for disposable products by virtue of the elimination of costs associated with the use of heated (high temperature) rollers and/or dryers to melt fibers and evaporate water;
- an ability to eliminate the use of specialty fusible bicomponent fibers and "hot melt" adhesives in the nonwoven web necessary for effecting adhesion of substrates to define regions therein and fix the location of superabsorbents; and,
- an ability to form embossed products which retain embossed markings without employing adhesives;

BRIEF DESCRIPTION OF THE SEVERAL VIEWS OF THE DRAWINGS

Not applicable.

DETAILED DESCRIPTION OF THE INVENTION

The nonwoven web incorporating the polymeric resin performs multiple functions in the process for making laminates for disposable goods and these primarily include supplying wet strength to the nonwoven web and supplying sufficient pressure sensitive adhesion to permit the nonwoven web to adhere to itself or to polymeric films and substrates employed in the manufacture of laminates for use in preparing disposable absorbent products. The use of these unique nonwoven webs permits one to alter the way such laminates are made in that one may eliminate some process steps and/or reduce energy requirements associated with the manufacture of the laminate products.

The nonwoven web is key to producing the laminates for disposable absorbent products contemplated herein. To form the laminate containing the superabsorbent within fixed location the nonwoven web should have sufficient pressure sensitive adhesive characteristics provided by the binder to provide a peel strength ranging from a low of about 50 g/5 cm to about 400 g/5 cm width and yet have a wet strength to provide a wet strength of at least 50 g/5 cm width. Preferably, the peel strength is within a range of 60 to 150 g/5 cm width and, if wet strength is a desired feature in the application, then the wet strength is at least 300 g/5 cm and typically at least 1000 g/5 cm width. When the nonwoven web has a peel strength within this range, the nonwoven web can be forced to adhere to itself under application of localized pressure (slightly better with the application of minimal heat) but at the same time be "delaminated from itself when wound into a large roll. The wet strength requirement is necessary to prevent disintegration under wet conditions. In some personal care applications that wet strength is not required. This wet strength is imparted through the crosslinkable functionality in the binder impregnated in the nonwoven webs. Too much crosslinking function tends to destroy the pressure sensitive characteristics of the nonwoven web thus rendering it unsuited for the process for preparing the laminate.

The nonwoven webs comprise a structure of fibers or filaments interlayed random fashion bonded together with a preferably, crosslinkable vinyl acetate/ethylene adhesive. A variety of processes have been used to prepare nonwoven webs and can be used in the preparation of the nonwoven webs described herein. These methods include air laying or wet laying, where the fibers are deposited upon a belt and a self-crosslinking vinyl acetate/ethylene adhesive sprayed over the surface of the fibers as it is passed along the belt. The fibers typically comprise wood pulp or a mixture of synthetic melt-fusible fibers, including rayon or other polymeric fibers. The nonwoven web is passed over a suction box which tends to pull the adhesive emulsion through the fibers to facilitate penetration and coating thereof. Often, the sheet is turned and an adhesive applied to the opposite surface of the fibrous bat while a suction is applied. The fibrous bat then is compressed between rollers and conveyed to a heated oven where the moisture is driven off and the adhesive cured. The polymer typically is incorporated in an amount to provide from 5 to 30%, preferably 10–25% by weight of the nonwoven web on a dry weight basis.

Crosslinkable acrylic and vinyl acetate/ethylene emulsions have been used heretofore in the preparation of nonwoven fabrics and have served to impart wet strength to disposable adsorbent products in conventional manner. In contrast to conventional prior art nonwoven webs, the acrylic or vinyl acetate/ethylene emulsion, for example, used for producing the nonwoven web is an acrylic emulsion polymer or a vinyl acetate/ethylene copolymer binder emulsion should have a viscosity in the range of 25 to 1000 cps @ 52% solids at 25° C. so that it may be appropriately sprayed onto the fibers and caused to penetrate and coat the fibers for enhanced adhesion. The vinyl acetate/ethylene copolymer is further characterized in that it has a vinyl acetate content of from 40 to 85 wt %, an ethylene concentration of from 15 to 60 wt. %, and a crosslinking monomer functionality, e.g., N-methylolacrylamide or its low formaldehyde derivative, i.e., the N-methylolacrylamide/acrylamide derivative in a 50/50 molar ratio. The $T_g$ is from −26 to −18° C. if adhesion is effected at room temperature (20–30° C). If minimal heat and lower roll pressures are employed, the $T_g$ can be from a higher $T_g$ polymer may be employed. Another key to the preferred vinyl acetate/ethylene/crosslinkable polymer emulsion is that it is prepared by emulsion polymerization in the presence of a low molecular weight polyvinyl alcohol having a degree of hydrolysis of from about 80 to 84% and a degree of polymerization of from 200 to 300. This viscosity range permits ease of application by spraying. Although stabilizing surfactants can be employed in the emulsion polymerization processes in amounts up to 10% by weight of the nonionic stabilizer, it is preferred, no surfactant is employed as surfactants may affect the wet strength of the web.

Acrylic emulsions stabilized with polyvinyl alcohol (PVOH) can be used for forming the laminates such as in the C-fold application. This polymer should contain 2–10 wt % poly(vinyl) alcohol based upon the weight of the monomers and with the alcohol having a hydrolysis value of from 96 to 98.8% and the degree of polymerization is the same as that used in forming the vinyl acetate/ethylene emulsions. The monomers can be such acrylates or methacrylates as butyl acrylate, 2-ethylhexyl acrylate, ethyl acrylate, methyl methacrylate, butyl methacrylate, etc. as known in the art and balanced to give a $T_g$ broadly between −26 and +18° C., if minimal heat is employed and −22 to −18 if adhesion is effected at room temperature.

The monomers for providing crosslinking functionality in either the acrylic or the vinyl acetate/ethylene polymers include N-methylolacrylamide, acrylamide, acrylamidobutyraldehyde dimethyl acetal, acrylamidobutyraldehyde diethyl acetal, acrylamidoglycolic acid, methyl acrylamidoglycolate, methyl acrylamidoglycolate methyl ether, acrylamidoglycolic acid methyl ester, iso-butyl methylol acrylamide or any other crosslinking monomer known in the art. The concentration of functional monomer in the polymer typically ranges from 0.5–6% by weight of the polymer, preferably 1–4%. The level may need to be adjusted within that range to accommodate variations in $T_g$ in order to optimize pressure sensitive adhesive properties.

The fiber component which form the nonwoven substrate base generally is comprised of cellulosic tissue, i.e., wood pulp having a basis weight from about 30 g/m² to 300 g/m², preferably 40 to 120 g/m². The wood pulp can be combined or bonded with other materials to form laminates, such as nonwoven-tissue, nonwoven-plastic (polyethylene or polypropylene) nonwoven-cellulosic, etc.

One key is that through the use of these nonwoven fibrous webs bonded with the unique vinyl acetate/ethylene polymers, pressure alone is sufficient to cause the nonwoven web or fabric to adhere to another substrate, typically itself, to provide adhesive bonds or adhesive lines which then have sufficient strength to maintain dry particulate, superabsorbent powders and cellulosic pulp within defined regions within the laminate. Another key is that under mild application of heat, i.e., temperatures far below those required for effecting adhesion via thermofusible bicomponent fibers, may be employed for higher $T_g$ polymers. Temperatures required for effecting adhesion in non woven webs incorporating essentially no thermofusible fibers component range from 60 to 100° C. Conventional temperatures required for effecting bonding of thermofusible bicomponent fibers range from about 105° C. and above. Elevation of temperature in the web to enhance adhesion is best achieved by use of a heat sealing bar heated to a temperature of not greater than about 250° C. for a time ranging up to a few seconds or through ultrasonic bonding techniques.

The liquid-absorbing agents which can be utilized in forming the disposable absorbent products include the common particulate water-absorbing polymeric absorbents. A host of superabsorbent materials are widely known in the art and can be employed here; representative examples are given in U.S. Pat. No. 4,960,477 and are incorporated by reference. Typically these are crosslinked polyacrylic acids and its salt, polysaccharides, starch, regenerated cellulose and derivatives thereof. Crosslinked polyacrylamides, crosslinked sulfonated polystyrenes, crosslinked poly(alkylene oxides) and alkyl-substituted phenyl ether, and others as described in U.S. Pat. No. 4,102,340 can also be employed and are incorporated by reference.

In accordance with one embodiment of the process, a high-capacity liquid absorbing laminate suitable for the fabrication of disposable absorbent soft goods is prepared by applying a metered amount of a dry, hydrophilic, polymeric absorbing agent to a substrate tissue or other material commonly used in the preparation of such liquid-absorbing laminates, enclosing the polymeric absorbing agent within the substrate and introducing the combined web into an embossing nip, calendar roll or caterpillar tread, (pressure roller) for providing indentations and defined regions in the laminate. One common method of forming the laminate is to deposit the particulate polymeric absorbents onto a moving, nonwoven web and then once the particulate polymeric absorbent is deposited on the web, another substrate, e.g., another nonwoven web is placed over the particulate polymeric absorbent and then the two substrates bonded together. When at least one of the nonwoven webs has the vinyl acetate/ethylene self crosslinking adhesive described herein, bonding points or lines can be effected through the localized pressure supplied by the pressure roller.

Another embodiment for producing absorbent particles is referred to as the C-fold process. In the C or e-fold process, a nonwoven web is carried upon a belt and the liquid-absorbing polymeric materials, e.g., the superabsorbents, powder or fiber or cellulose pulp, added generally toward the middle portion of the web as it proceeds along the belt. The side portions of the nonwoven web then are folded inwardly toward the center or longitudinal axis of the web in overlapping manner and then passed under the pressure roller. Again, because of the unique acrylic and vinyl acetate/ethylene binders employed in the bonding of the nonwoven web, pressure of the pressure roller alone which is used to provide indentations within the now-folded web causes the nonwoven web to adhesively adhere to its surface and provide bonding points or lines. Accordingly, the liquid-absorbing polymeric material or cellulosic pulp is fixed within the folds of the nonwoven web. The resulting laminate then can be incorporated into a final product by, converters (down stream manufacturers) wherein the laminate comprising the nonwoven web containing the polymeric superabsorbent is combined with other components to generate a disposable product, such as a disposable diaper, etc.

Adhesion of the nonwoven web to itself or another substrate is effected by means of pressure applied to the nonwoven web via embossing nips or ultrasonic bonding techniques. These pressure rollers e.g., nip rolls, as they are sometimes called, are rollers having a tooth-like surface which form indentations in the nonwoven web as the web passes under the pressure roller. When using the nonwoven webs described herein, at rolling nip pressures of from about 10 to in excess of 100,000 lbs/in$^2$, preferably within 50 to 50,000 lbs/in$^2$, the web incorporating the acrylic, vinyl acetate/ethylene or crosslinkable acrylic or vinyl acetate/ethylene adhesive bonds between the surfaces of the web, thereby defining regions within the web and thus fixing the location of the hydrophilic polymeric absorbing materials within the laminate formed from the web. Lower pressures may be used if some heat is employed. Also, the nonwoven web allows for the retention of embossed and decorative surfaces due to the reduced hysteresis of the self crosslinking vinyl acetate/ethylene adhesive. Recall that earlier processes required the application of an additional adhesive, the addition of water to tackify the polymeric absorbents or adhesives or excess heat to effect adhesion of the nonwoven web through the melt fusion of thermoplastic polymeric fibers and or hot melt adhesives.

The following examples are provided to illustrate various embodiments of the invention and are not intended to restrict the scope thereof.

EXAMPLE 1

Preparation of Nonwoven Emulsion

General Procedure a) To a one-gallon pressure reactor is charged 400.0 g of distilled water, 760.0 g of a 10% aqueous solution of Airvol 203 polyvinyl alcohol, 15.0 g of acetic acid, 4.0 g of a 5% aqueous solution of ferrous ammonium sulfate and 1.09 g of phosphoric acid. To this is added 246.6 g of vinyl acetate. The agitator is turned on to 1000 rpm and the temperature is raised to 40° C. Once the temperature has stabilized, 650 g of ethylene is added over 15 minutes and 17.2 g of a 15.0% aqueous solution of sodium formaldehyde sulfoxylate is added. To this heated mixture is added a 0.8% solution of hydrogen peroxide at a rate of 0.1 ml/min.

Once the reaction is initiated, the 15.0% aqueous solution of sodium formaldehyde sulfoxylate is added at 0.3 ml/min. Ten minutes later, 229 g of a 32% aqueous solution of N-methylolacrylamide (NMA) is added at a rate of 1.09 g/min. At the 30 minute mark from initiation, 735.0 g of vinyl acetate is added at a rate of 4.6 g/min. The temperature and pressure is maintained throughout the reaction until the 3 hour and 15 minute mark, whereupon the pressure is allowed to decay. When the N-methylolacrylamide delay is complete, the hydrogen peroxide delay is shut off and a delay of 5% aqueous t-butyl hydroperoxide is added at 2.0 g/min. When the free vinyl acetate level is below 2.0%, the reactor is cooled to 35° C. and the emulsion is transferred to the degasser.

The composition of the copolymer was estimated from monomer input to the reactor and comprised 63% vinyl acetate, 32.3% ethylene and 4.7% N-methylolacrylamide (NMA). The emulsion had a solids content of 47.1%, 732 cps viscosity with a Brookfield LV viscometer at 60 rpm. The Tg was −25° C.

EXAMPLE 2

A series of laminates were prepared using a C-fold procedure from a variety of nonwoven webs which incorporated different acrylate, vinyl acetate and crosslinkable polymers with the crosslinkable, vinyl acetate/ethylene prepared in accordance with the general procedure of Example 1. Super absorbents were laid onto the nonwoven web and the web folded over upon itself. The nonwoven webs were fabricated into laminates with the super absorbent embedded into rectangular squares or patterns consisting of small squares formed under a roll pressure of 50,000 lbs./in$^2$. The resulting laminates were evaluated for peel strength at the juncture points and wet strength.

Table 1 provides the following conditions and results.

TABLE 1

| Run | Tg deg C. | B.W. g/m$^2$ | Thickness mm | Abs. g/g | Rate g/g/sec | Dry CD g/5 cm | Wet CD g/5 cm | Peel g/5 cm |
|---|---|---|---|---|---|---|---|---|
| 1 | −15 | 90.3 | 2.5 | 11.8 | 0.77 | 1964 | 1329 | 0 |
| 2 | −26 | 98 | 2.1 | 11.3 | 0.74 | 1688 | 1168 | 61 |
| 3 | −20 | 95.8 | 1.9 | 10.1 | 0.64 | 1907 | 1175 | 61 |
| 4 | −20 | 95.9 | 2.1 | 11.3 | 0.66 | 1769 | 1174 | 23 |
| 5 | −25 | 96.7 | 2.8 | 11.2 | 0.74 | 1837 | 778 | 94 |
| 6 | (−15) & (+30) | 95.2 | 2.3 | 9.1 | 0.04 | N/D | N/D | 4 |
| 7 | 4 | 95.1 | 2.5 | 11.8 | 0.71 | 1566 | 576 | 344 |
| 8 | −45 | 95.0 | 2.1 | 0 | 0 | 788 | 233 | 492 |
| 9 | −23 | 89 | 2.3 | 10.6 | .63 | 815 | 1312 | 371 |

| Run | Polymer Type | % VAM | % Ethylene | % NMA |
|---|---|---|---|---|
| 1. | VAE −15° C. | 70 | 30 | 3 |
| 2. | VAE −26° C. | 60 | 40 | 1 |
| 3. | VAE | 60 | 40 | 1 |
| 4. | VAE | 60 | 40 | 1 |
| 5. | PVOH stabilized | VAE | No | Stabilizer |
| 6. | Blend a −15° C. | VAE and | a 30° C. | acrylic |
| 7. | Commercial VAE | 80 | 20 | 0 |

TABLE 1-continued 8. emulsion is a carboxylated acrylic emulsion sold under the trademark Flexcryl 1625.
9. Acrylic PVOH is a methyl methacrylate/butyl acrylate emulsion stabilized with polyvinyl alcohol.

"B.W." refers to "The Basis Weight" of the sample was measured by TAPPI Standard Method "T410 om-93".
"Abs" refers to the amount of water absorbed by 1 gram of laminate sample.
Rate refers to speed of fluid uptake in grams of water per gram laminate per second.

Dry CD (Dry Tensile test) is based on TAPPI Standard Method "T494 om-88" called "Tensile Breaking Properties Of Paper And Paperboard (Using Constant Rate Of Elongation Apparatus" is measure by in the cross-direction (CD). The only modification to this test is that a 2 inch wide (5 cm)×10 inch long (25 cm) sample rather than 1 inch wide (2.5 cm)×10 inch long (25 cm) sample is employed.

Wet CD (Wet strength Wet Tensile Test) is based on TAPPI Standard Method "T456 om-87" called "Wet Tensile Breaking Strength Of Paper And Paperboard". A 2 inch wide sample (5 cm) rather than a 1 inch wide sample is employed in the procedures described herein.

Peel refers to "peel test" that is a modification of the peel test method known in industry as PSTC-1 called "Peel Adhesion For A Single Coated Pressure-Sensitive Tapes 180 Degree Angle". The description of the test is published in a book called Test Methods for Pressure Sensitive Tapes by the Pressure Sensitive Tape Council (9th edition). This test also known in the industry as the "T-Test" to specify that the test is carried out to measure the adhesion of the substrate to itself rather than a release paper; the other modification employed in the test results described herein in that the test is based upon a 90 degree peel rather than a 180 degree peel.

The results show that nonwoven webs impregnated with crosslinkable vinyl acetate/ethylene emulsion polymers having peel strengths of at least 50 g/5 cm permitted the formation of laminates with acceptable bonding points. The results show that good peel strength is not enough and can be too high (above 350) as for example in run 8. These laminates would not unwind from a roll and delaminate upon unwinding thereby rendering the laminates unusable. Run 8 also was unacceptable because of the poor absorbency value. Note the $T_g$ was below the desired level. In some applications, the wet strength must be at least 100. The peel strength must be sufficient for forming the laminate by the procedure described herein using localized pressure optionally with minimal heat to form the adhesive bonds or lines for defining regions for retaining the superabsorbents.

EXAMPLE 3

The procedure for preparing laminates in accordance with the procedure of Example 2 was followed except that the rollers were maintained at a temperature of 20 to 30° C. and the roll pressure was reduced to 60 psig for runs A–D. Run E was conducted at a roll temperature of 100° C. The contact time was approximately 3 seconds which resulted in raising the localized temperature at the point of contact to about 95° C. The results are set forth in Table 2.

TABLE 2

Peel Strength as a Function of Chemical Modifications

| Sample ID | "T"-Peel Strength g/5 cm | Absorption Capacity g/g | Absorbency Rate g/g/sec. | Strength (Dry CD) g/5 cm | Strength (Wet CD) g/5 cm | Roll Temp. |
|---|---|---|---|---|---|---|
| A | 0   | 12 | 0.75 | 1960 | 1109 | 20° C. |
| B | 45  | 12 | 0.74 | 1621 | 565  | 20° C. |
| C | 153 | 11 | 0.78 | 1665 | 281  | 20° C. |
| D | 200 | 11 | 0.82 | 1089 | 141  | 20° C. |
| E | 361 | 11 | 0.8  | 1182 | 191  | 100° C. |

A has 76% vinyl acetate, 20% ethylene, 4% N-methylolacrylamide and a Tg of 0° C.
B has 77% vinyl acetate, 22% ethylene, 1% N-methylolacrylamide and a Tg of 0° C.
C has 77% vinyl acetate, 22.5% ethylene, 0.5% N-methylolacrylamide and a Tg of 0° C.
D has 82% vinyl acetate, 18% ethylene, 0% N-methylolacrylamide and a Tg of 4° C.
E has 82% vinyl acetate, 18% ethylene, 0% N-methylolacrylamide and a Tg of 4° C.

The results show that the application of minimal heat to the process for forming C-fold products results in good dry and wet cross-directional tensile strengths. Runs D and E show little wet strength as would be expected. However, in many cases wet strength is not of paramount importance. T-peel values did increase with reduced levels of NMA crosslinker and with a mild application of heat as shown in Run E.

What is claimed is:

1. In a process forming a laminate suited for use in preparing disposable absorbent products by
    overlaying a substrate over the particulate polymeric absorbent and thereby forming a laminate trapping the polymeric absorbent between said first nonwoven fibrous web and said substrate;
    passing the laminate having the polymeric absorbent trapped between the first nonwoven web and second substrate through pressure roll means for imparting indentations in the laminate; and then,
    adhesively bonding the first nonwoven web and overlaid substrate at a plurality of points thereby forming discrete regions within the laminate and thus fixing a portion of the polymeric absorbent within said regions,
    the improvement which comprises:

adhesively bonding the first nonwoven fibrous web to said overlaid substrate solely by means of the pressure supplied by said roller means and effecting adhesion through the polymeric resin utilized in bonding the fibers in the web and said adhesion effected without the addition of water or heat sufficient to raise the adhesive temperature above about 100° C.

2. The process of claim 1 wherein the polymeric resin is capable of effecting a pressure sensitive adhesiveness sufficient to impart from 50 to 400 g/5 cm peel strength in a nonwoven web consisting essentially of wood pulp as the fiber component after having a pressure applied by said pressure roll means of from 1000 to 100,000 lbs/in$^2$.

3. The process of claim 2 wherein the polymeric resin is a vinyl acetate/ethylene polymer that is crosslinkable and is capable of imparting a wet strength of at least 50 g/5 cm in the resulting laminate.

4. The process of claim 3 wherein the binder is a crosslinkable vinyl acetate/ethylene polymer having a Tg of from −26 to +18° C.

5. The process of claim 4 wherein the crosslinkable component is N-methylolacrylamide and is present in a range from 1–4% by weight of the copolymer.

6. In a C-fold e-fold process for forming a laminate suited for use in preparing disposable absorbent products which comprises:

depositing polymeric absorbent onto a first nonwoven fibrous web bonded with a crosslinked polymeric resin;

folding the side portions of the nonwoven web inwardly toward the center along the longitudinal axis of the web in overlapping manner thereby forming a laminate trapping the polymeric absorbent within the fold of said nonwoven fibrous web;

passing the laminate having the polymeric absorbent trapped within the fold of the nonwoven web through a pressure roller for defining imparting indentations in the laminate; and then, adhesively bonding the thus formed laminate formed from the first nonwoven web at a plurality of points thereby forming discrete, sealed regions within the laminate and thus fixing a portion of the polymeric absorbent within said regions, the improvement which comprises:

adhesively bonding the laminate solely by means of the pressure supplied by said pressure roller and effecting said adhesive bonding through the polymeric resin in the nonwoven web without the addition of water, said pressure rolls maintained at a temperature below about 250° C. and the contact time between the rollers and nonwoven web such that the temperature of the adhesive in the nonwoven web does not exceed about 100° C.

7. The process of claim 6 wherein the polymeric emulsion is capable of effecting a pressure sensitive adhesiveness sufficient to impart from 50 to 400 g/5 cm peel strength in a nonwoven web consisting essentially of wood pulp as the fiber component.

8. The process of claim 7 wherein the crosslinked polymeric resin is a vinyl acetate/ethylene polymer that has crosslinkable functionality capable of imparting a wet strength of at least 300 g/5 cm in the resulting laminate.

9. In a process forming a laminate suited for use in preparing disposable absorbent products by depositing particulate polymeric absorbents onto a first nonwoven fibrous web, the fibers bonded with a polymeric resin;

placing a second substrate over the particulate polymeric absorbent and thereby forming a laminate trapping the polymeric absorbent between said first nonwoven fibrous web and said substrate;

passing the laminate having the polymeric absorbent trapped between the first nonwoven web and second substrate through pressure roll means for imparting indentations in the laminate; and then, adhesively bonding the first nonwoven web and second substrates at a plurality of points thereby forming discrete regions within the laminate and thus fixing a portion of the polymeric absorbent within said regions, the improvement which comprises:

utilizing a vinyl acetate/ethylene polymer having a $T_g$ of from −22 to −18° C.; and, applying pressure by said roller means at a temperature of from 20 to 30° C. and thereby effecting adhesion through the polymeric resin used to bond the fibers within the web.

* * * * *